United States Patent
Åkerfeldt

(10) Patent No.: US 7,445,625 B2
(45) Date of Patent: *Nov. 4, 2008

(54) INTERNAL TELESCOPIC GUIDE FOR AN INFLATABLE AIR CUSHION

(75) Inventor: Dan Åkerfeldt, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 443 days.

This patent is subject to a terminal disclaimer.

(21) Appl. No.: 11/048,067

(22) Filed: Feb. 2, 2005

(65) Prior Publication Data

US 2005/0192625 A1  Sep. 1, 2005

Related U.S. Application Data

(63) Continuation-in-part of application No. 10/209,974, filed on Aug. 2, 2002, now Pat. No. 7,247,163.

(51) Int. Cl.
*A61B 17/00* (2006.01)
(52) U.S. Cl. .................. 606/203; 606/201; 602/53
(58) Field of Classification Search ............ 606/201, 606/203; 602/53
See application file for complete search history.

(56) References Cited

U.S. PATENT DOCUMENTS

| | | | |
|---|---|---|---|
| 3,797,853 A | 3/1974 | Bendl et al. | |
| 5,307,811 A | 5/1994 | Sigwart et al. | |
| 5,542,427 A | 8/1996 | Åkerfeldt | |
| 5,792,173 A | 8/1998 | Breen et al. | |
| 6,066,157 A | 5/2000 | Barbere | |
| 6,174,306 B1 * | 1/2001 | Fleischmann | 604/543 |
| 6,503,266 B1 | 1/2003 | Sjoegren et al. | |
| 2004/0024417 A1 | 2/2004 | Akerfeldt | |

FOREIGN PATENT DOCUMENTS

| | | |
|---|---|---|
| EP | 0 462 088 B1 | 11/1995 |
| EP | 1 386 586 A1 | 2/2004 |
| SU | 1386172 A1 | 4/1988 |
| WO | WO 94/05221 A1 | 3/1994 |
| WO | WO 98/34547 A1 | 8/1998 |
| WO | WO 01/85062 A1 | 11/2001 |

\* cited by examiner

*Primary Examiner*—Darwin P Erezo
(74) *Attorney, Agent, or Firm*—Foley & Lardner LLP

(57) ABSTRACT

The invention provides an air cushion unit (4) for use in conjunction with a compression device for stopping bleeding from puncture wounds. The air cushion unit (4) comprises a base plate (5), an inflatable air cushion (6), which is attached to the base plate (5), and an internal telescopic guide (7), connecting the base plate (5) with the top of the air cushion (6). Throughout the pressurizing of the inflatable air cushion (6), the length of the telescopic guide (7) corresponds to the degree of expansion of the air cushion (6), thereby providing an internal support for the air cushion unit (4), which eliminates undesired, irregular movements of the air cushion (6).

4 Claims, 3 Drawing Sheets

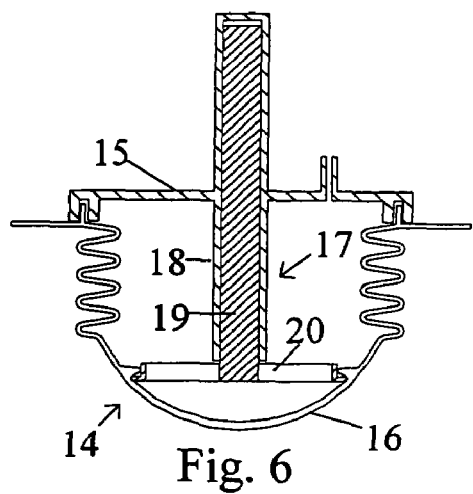
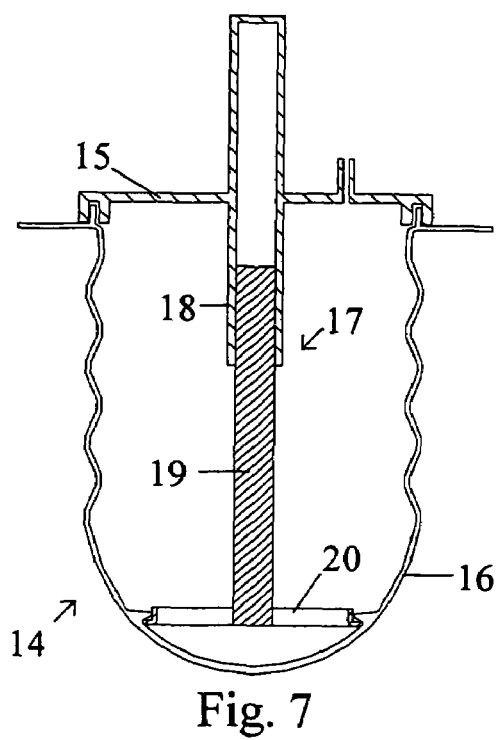

INTERNAL TELESCOPIC GUIDE FOR AN INFLATABLE AIR CUSHION

This application is a continuation in part of U.S. application Ser. No. 10/209,974, filed Aug. 2, 2002, now U.S. Pat. No. 7,247,163, whose entire contents are incorporated herein by reference.

FIELD OF THE INVENTION

The present invention relates generally to air cushion units used in conjunction with compression devices for stopping bleeding from puncture wounds, and in particular to an inflatable air cushion unit being provided with a telescopic guide which ensures that the air cushion during pressurizing unfolds regularly, thereby preventing the contact area of the air cushion from moving away from the wound site.

BACKGROUND OF THE INVENTION

The present invention is an improvement of the air cushion units disclosed in the present applicant's WO 94/05221, U.S. Pat. No. 5,542,427 and WO 98/34547 publications, where the latter discloses air cushions provided with a reinforcement portion. The air cushion unit according to these publications includes a base plate, the upper side of which is attached to the arch of a femoral compression device, such as the femoral compressor disclosed in EP 0 462 088 and U.S. Pat. No. 5,307,811, which are assigned to the present assignee. On the base plate there is an inflatable air cushion, which is mounted by gluing or fusing along the circumference of the base plate to provide an airtight sealing between the air cushion and the base plate. The cushion is made of a material that is folded such that the air cushion when not inflated, i.e. when it is packaged, occupies as little volume as possible.

A potential problem with these prior art air cushions is that during the pressurizing phase they have a tendency to unfold unevenly, i.e. the folds do not unfold continuously and regularly but stepwise in an irregular way. These irregular movements of the air cushion during pressurizing may move the entire compression device away from its correct position over the femoral or other artery, which may cause unnecessary bleeding. The irregular behavior of a compression device provided with such an air cushion unit may also give an inexperienced user a feeling that something is wrong, which—besides being uncomfortable in itself—may call for frequent checks that everything is in order, which extends the pressurizing time and may cause extra bleeding. Another problem is that the air cushion when in a semi-inflated state has a tendency to behave like a ball joint in such a way that the centre of the cushion surface moves around the wound site. In the worst case, this ball-joint movement may cause the air cushion to roll off the wound site, which again gives rise to unnecessary bleeding.

SUMMARY OF THE INVENTION

The object of the present invention is therefore to provide an improved air cushion unit that during pressurizing unfolds in a regular way without any undesired movements, which makes a compression device provided with such an air cushion unit more user-friendly and eliminates the risk that the air cushion moves away from the wound site.

This object is achieved by providing an improved air cushion unit, preferably of a single use type, for use together with a femoral (or other artery or vessel) compressor. The air cushion unit, which is to be attached to the arch (or other stiff or flexible member such as a strap) of the femoral compressor, comprises a base plate and an inflatable air cushion attached to the base plate. According to the present invention, the air cushion unit is provided with a telescopic guide, which is arranged inside the air cushion and extends from the base plate to the top of the air cushion.

BRIEF DESCRIPTION OF THE DRAWINGS

FIG. 6 is a cross-sectional view of a second embodiment of an air cushion unit according to the present invention.

FIG. 7 is a cross-sectional view of the air cushion unit of FIG. 6 in an inflated state.

DESCRIPTION OF THE INVENTION

The air cushion unit according to the present invention has the same basic design as the ones disclosed in the above referenced WO 94/05221 or WO 98/34547, the main difference being that the air cushion disclosed in WO 98/34547 is provided with a reinforcement portion integral with the cushion surface. For the sake of simplicity, the air cushion according to the present invention as well as the air cushion according to prior art are described and illustrated without this reinforcement portion, but it should be understood that such a reinforcement portion could be provided also for the present air cushion.

Figure 1:
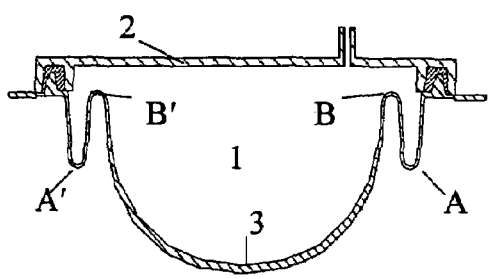
FIG. 1 is a cross-sectional view of a prior art air cushion unit.

A prior art air cushion unit 1 is illustrated in cross-section in FIG. 1 and comprises a base plate 2, on which an inflatable air cushion 3 is mounted by gluing or fusing along the periphery of the base plate 2. In use, the base plate 2 is attached to the arch (or other portion) of a femoral (or other vessel) compressor, such as the one disclosed in EP 0 462 088 and U.S. Pat. No. 5,307,811. The attachment of the cushion unit 1 to the femoral compressor is done by a snap attachment, which is fully disclosed in the above mentioned application WO 94/05221, and will therefore not be described herein. FIG. 1 shows the air cushion unit 1, which preferably is a replaceable and single use unit, in a state before use, wherein the material from which the air cushion 3 is made is folded at A, A' and B, B', so that the air cushion unit 1 occupies as little volume as possible.

Figure 2:
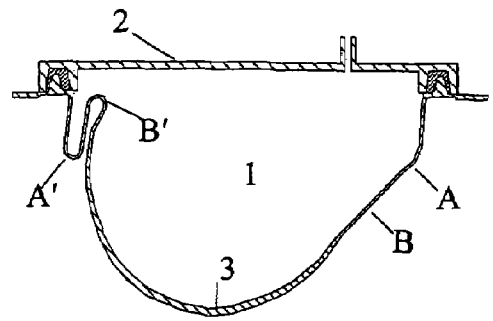
FIG. 2 is a cross-sectional view of the air cushion unit of FIG. 1 in a semi-inflated state, and illustrates the irregular unfolding of the air cushion.

FIG. 2 shows the air cushion 3 in a semi-inflated state, and illustrates the above-mentioned problem that the prior art air cushion 3 during pressurizing unfolds irregularly, which—in this particular case—makes the air cushion 3 to adapt the deformed shape shown in the figure, where the folds at A, B have been unfolded while the folds at A', B' still are intact. The irregular behavior of the air cushion 3 is also transmitted to a femoral compressor on which the air cushion unit 1 is attached, which in the worst case may cause the femoral compressor to move away from its correct positioning over the femoral artery, thereby causing unnecessary bleeding.

Even though the risk that the femoral compressor actually moves during inflation in pratice has proven to be very small, a non-negligible disadvantage with the irregular and stepwise expansion of the air cushion 3 is that it may give an inexperienced user (e.g. a nurse or a doctor) the impression that something is going wrong during the inflation procedure, which, in turn, calls for frequent (and mostly unnecessary) checks that everything is in order.

Figure 3:
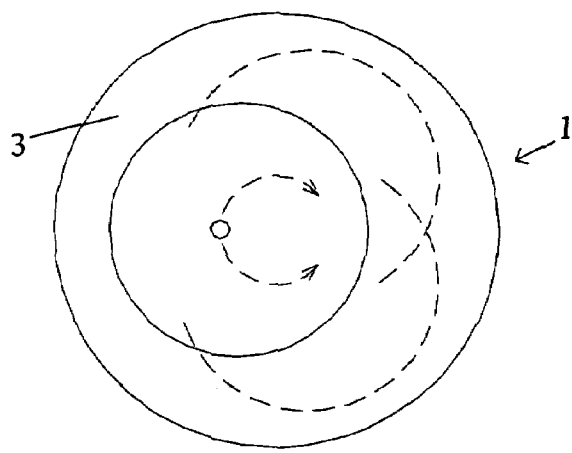
FIG. 3 illustrates schematically the ball-joint movement of a semi-inflated air cushion according to prior art.

FIG. 3 is a schematic top view of the prior art air cushion unit 1 in a semi-inflated state, and illustrates schematically the above-mentioned problem that the air cushion 3 when in a semi-inflated state can move like a ball joint in that the top surface of the air cushion 3 moves around the centre of the air cushion 3. This ball joint movement, which may be in the clockwise or counter-clockwise direction, is indicated by dashed lines and by the double-arrow C. In the worst case, this undesired movement may cause the air cushion 3 to slip away from its correct positioning at the puncture site, which again leads to unnecessary bleeding or at least to additional checks that the femoral compressor, on which the air cushion unit 1 is attached, is correctly positioned at the femoral artery.

In general terms, the invention resides in connecting the air cushion and the base plate with a telescopic guide structure, having sufficient rigidity, such that when inflated, the drawback with the prior art devices of being subject to a risk of uneven unfolding, or of the tendency of moving around the wound site is reduced or even eliminated.

Figure 4:
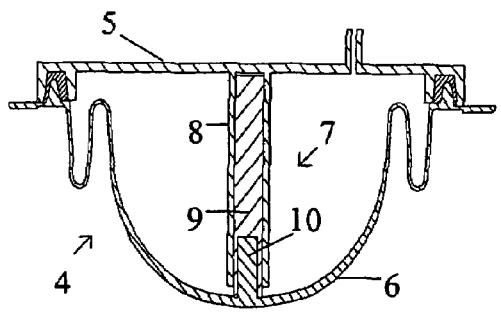
FIG. 4 is a cross-sectional view of an air cushion unit according to the present invention.
Figure 8:
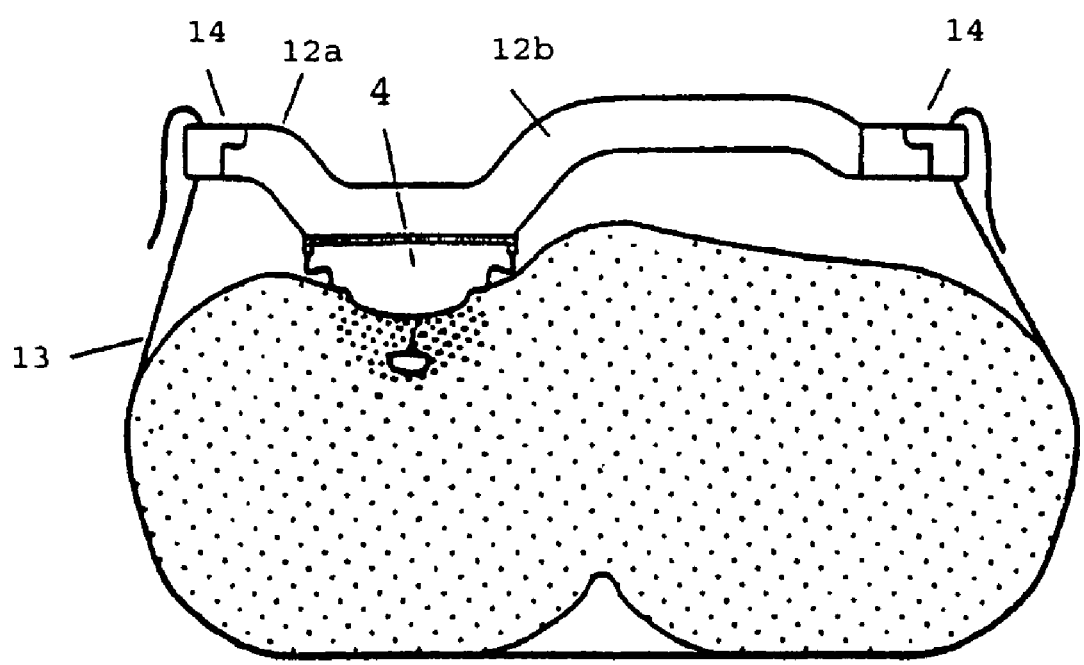
FIG. 8 is a cross-sectional view of an air cushion unit being applied to a patient.

In FIG. 4 is illustrated an air cushion unit 4 according to the present invention. The air cushion unit 4 comprises a base plate 5 and an air cushion 6, which —as in the prior art design —may be and preferably is attached to the base plate 5 by gluing or fusing along the periphery of the base plate 5. As before, the air cushion unit 4 is designed for attachment to the arch (or other portion) of a femoral (or other vessel) compressor, such as the compressor disclosed in EP 0 462 088 and U.S. Pat. No. 5,307,811. The attachment can be releasable as described in, for example, WO 94/05221. However, it is also possible and within the scope of the invention to provide an integrated device where arch and cushion are made in one piece. FIG. 8 shows the air cushion unit 4 attached to a patient by an arch formed by two extensions 12a and 12b. The extensions are fastened to a belt 13 via fasteners (such as a self locking device) 14.

In contrast to the prior art air cushion unit 1 described above, the air cushion unit 4 comprises also an internal telescopic guide 7. The telescopic guide 7, which is inside the air cushion 6 and extends from the base plate 5 to the top of the air cushion 6, comprises a first rod 8 and a second rod 9 arranged in a sliding relation to each other, said first rod acting as a guiding member for said second rod. In the embodiment shown in FIG. 4, the first rod 8, which extends from the base plate 5, is hollow and is made integrally with the base plate 5, while the second rod 9, which extends from the top of the air cushion 6 and into the hollow first rod 8, is attached to the air cushion 6 by a pin 10, which projects a short distance into the otherwise solid second rod 9. The inner diameter of the first rod 8 is approximately equal to the diameter of the second rod 9.

Figure 5:
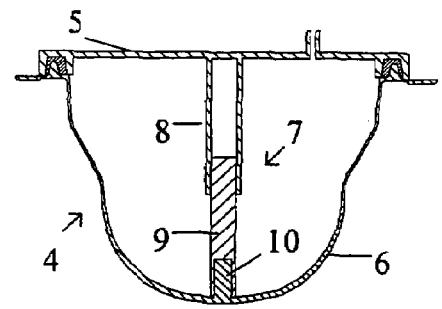
FIG. 5 is a cross-sectional view of the air cushion unit of FIG. 4 in an inflated state, and illustrates the regular unfolding of the air cushion.

FIG. 5 shows the air cushion 6 in an inflated state, and illustrates that the air cushion 6 during pressurizing unfolds in a continuous and regular way. As can be seen from FIG. 4 and FIG. 5, the second rod 9 can telescope into and out from the first rod 8, thereby providing the telescopic guide 7 with a variable length that corresponds to the degree of expansion of the air cushion 6. Thus, when the air cushion 6 is not inflated, such as when the air cushion unit 4 is packaged, the second rod 9 of the telescopic guide 7 is completely, or almost completely, telescoped into the first rod 8, and when the air cushion 6 is inflated, the second rod 9 projects out from the first rod 8, i.e. the guide 7 is telescoped. Due to the variable length of the internal telescopic guide 7, the air cushion 6 is provided with a support that acts throughout the pressurizing of the air cushion 6. Providing the air cushion unit 4 with the internal telescopic guide 7 therefore prevents the irregular unfolding of the air cushion 6 and eliminates the possibility of any ball joint movements of the air cushion 6.

FIG. 6 and FIG. 7 illustrate a second embodiment of an air cushion unit 14 according to the present invention. In FIG. 6, the air cushion unit 14 is shown in a collapsed state, while FIG. 7 illustrates the air cushion unit 14 in an expanded state. The air cushion unit 14 comprises a base plate 15 and an air cushion 16, which is attached to the base plate 15 by gluing or fusing along the periphery of the base plate 15. As before, the air cushion unit 14 is designed to be attached to the arch (or other portion) of a femoral (or other vessel) compressor, such as the compressor disclosed in EP 0 462 088 and U.S. Pat. No. 5,307,811. As can be seen from a comparison of FIG. 4 and FIG. 6, the air cushion 16 of FIG. 6 differs from the air cushion 6 of FIG. 4 in that the former has a bellows-like shape. The air cushion unit 14 further comprises a telescopic guide 17, which comprises a first rod 18 and a second rod 19. In this embodiment, the first rod 18 is hollow and is made integrally with the base plate 15 in such a way that the first rod 18 protrudes from both sides of the base plate 15. The second rod 19 is attached a small distance from the top of the air cushion 16 and can telescope into and out from the first hollow rod 18. Because of the extension of the first rod 18 on the backside of the base plate 15, i.e. on the side opposite to the air cushion 16, the first rod 18 can be made longer than the cross-sectional height of the air cushion 16 when in a collapsed state, which, in turn, means that the effective length of stroke for the telescopic guide 17 is increased. Notwithstanding the fact that the first rod 18 extends also from the backside of the base plate 15, the actual guidance of the air cushion 16 is performed primarily from the inside of the air cushion 16, and herein also the telescopic guide 17 is referred to as an internal telescopic guide 17.

The embodiments illustrated in the drawings both comprise cylindrical rods making up the telescopic guide means. However, it is within the inventive concept to design the guide means in many other ways, such as with rods having other cross-sections, e.g. square, rectangular, cross-shaped, etc. Also, it is not strictly necessary that the hollow rod member entirely encloses the first rod that runs inside the hollow rod. Instead, e.g. for a square rod, it is possible to make a guiding structure of e.g. plane parallel walls in sliding contact with the first rod. These walls can be provided with edges that prevent the sliding rod member from deflecting laterally.

For the purpose of the present invention, the most important feature of the embodiment illustrated in FIG. 6 and FIG. 7 is, however, the attachment of the second rod 19 near the top of the air cushion 16. At the top end of the second rod 19, i.e. at the end that faces the air cushion 16, the second rod 19 is provided with a ring-shaped member 20, which is attached to the inner wall of the air cushion 16, such that a small distance is provided between the top of the air cushion 16 and the top end of the second rod 19. The advantage of the radially enlarged attachment area that is provided by means of the ring-shaped member 20 is an enhanced stability for the air cushion unit 14 as well as further increased resistance against the ball joint movements that could occur with an air cushion unit according to the prior art. Further, because of the distance between the top end of the second rod 19 and the top of the air cushion 16, the top portion of the air cushion 16 is still soft and pliable, which is comfortable for a patient and counteracts any tendency of the air cushion unit 16 to roll off its correct position at a puncture site.

Before finishing the description of the operation of the telescopic guide, a few comments can be made. It should be understood that other ways of attaching the rods to the base plate and air cushion, respectively, could be employed. For example, the second rod could be inserted in a recess formed in the inner surface of the air cushion, or the second rod as well as the first rod could be attached to the air cushion and base plate, respectively, by gluing. It is also possible to let the rod that extends from the air cushion to be hollow, so that the other rod, which extends from the base plate, can be inserted therein. The important feature is that the air cushion unit according to the present invention is provided with an internal telescopic guide having a variable length that corresponds to the degree of expansion of the air cushion. For this purpose, it is also conceivable that the telescopic guide, as an alternative, comprises more than two rods that can telescope into and out from each other. On the other hand, the maximum length of the telescopic guide should well cover the cross-sectional height of the completely inflated air cushion, so that a small overlap exists between the ends of the rods, thereby providing a stable and inflexible construction for the internal telescopic guide.

Although the present invention has been described with reference to specific embodiments, also shown in the appended, drawings, it will be apparent for those skilled in the art that many variations and modifications can be done within the scope of the invention as described in the specification and defined with reference to the following claims. For example, the guide may include at least three rods, the rods having increasing diameters, wherein at least two of the rods are hollow, and a rod having a smaller diameter is slidably positioned inside a rod having a larger diameter, so that telescopic action is achieved. As another example, the cushion may be inflated or filled with gases other than air, or with liquid(s).

What is claimed is:

1. An inflatable cushion assembly to apply pressure to a patient, comprising:
   a base plate,
   an inflatable cushion adapted to apply pressure to a wound, the inflatable cushion defining an enclosed interior space which is configured to be pressurized,
   two extensions connected to the base plate,
   at least one belt fastener, connected to at least one of the extensions, for receiving a belt to hold the inflatable cushion against the patient, and
   a telescopic guide at least partly inside the interior space, and coupled to, the cushion,
   wherein the telescopic guide expands in a direction perpendicular to the base plate when the interior space is pressurized,
   wherein an end of the telescopic guide is attached to the inflatable cushion at a portion away from a top portion of the inflatable cushion.

2. An inflatable cushion assembly as set forth in claim 1, wherein the end of the telescopic guide is attached to the inflatable cushion via a ring-shaped member.

3. An inflatable cushion assembly as set forth in claim 1, wherein the telescopic guide extends a distance away from the base plate on a side of the base plate that is opposite to the inflatable cushion.

4. An inflatable cushion assembly as set forth in claim 1, further comprising a device to releasably attach the base plate to the two extensions.

\* \* \* \* \*